(12) United States Patent  
Cantor et al.

(10) Patent No.: US 8,983,856 B1  
(45) Date of Patent: Mar. 17, 2015

(54) SCHEDULING ASSESSMENTS FOR DETERMINING RISK ADJUSTMENT PAYMENT INFORMATION

(71) Applicant: Community Care Health Network, Inc., Scottsdale, AZ (US)

(72) Inventors: Michael A. Cantor, Scottsdale, AZ (US); George S. Chen, San Diego, CA (US); Alan A. Garcia, Phoenix, AZ (US); Theodore T. Kyi, San Diego, CA (US); David J. Watson, Carrollton, TX (US)

(73) Assignee: Community Care Health Network, Inc., Scottsdale, AZ (US)

( * ) Notice: Subject to any disclaimer, the term of this patent is extended or adjusted under 35 U.S.C. 154(b) by 41 days.

(21) Appl. No.: 14/142,496

(22) Filed: Dec. 27, 2013

(51) Int. Cl.
*G06Q 50/22* (2012.01)
*G06Q 10/10* (2012.01)
*H04M 3/487* (2006.01)

(52) U.S. Cl.
CPC ............ *G06Q 50/22* (2013.01); *G06Q 10/1095* (2013.01); *H04M 3/4878* (2013.01)
USPC .............................................................. 705/2

(58) Field of Classification Search
None
See application file for complete search history.

(56) References Cited

U.S. PATENT DOCUMENTS

| 2008/0059227 | A1* | 3/2008 | Clapp | 705/2 |
| 2010/0070296 | A1* | 3/2010 | Massoumi et al. | 705/2 |
| 2013/0138449 | A1* | 5/2013 | Piot | 705/2 |
| 2013/0304484 | A1* | 11/2013 | Martinez et al. | 705/2 |

* cited by examiner

*Primary Examiner* — Valerie Lubin
(74) *Attorney, Agent, or Firm* — Fish & Richardson P.C.

(57) ABSTRACT

A computer-implemented method includes, in one aspect, identifying, in a data repository, (i) information indicative of a health care provider who is assigned to a pre-defined calling zone, and (ii) radius information; accessing scheduling information that comprises a plurality of time slots, wherein each time slot corresponds to a time for the health care provider to perform the health risk assessment; selecting, by one or more computer systems, a particular slot from the scheduling information; for the selected slot, applying a geo-dialing algorithm to candidate information that is indicative of one or more members of one or more health plans who are candidates for scheduling in the selected time slot; identifying, based on application of the geo-dialing algorithm, a candidate with a geographic location that is a decreased distance from a geographic location of the health care provider; and causing a call to be placed to the identified candidate.

15 Claims, 12 Drawing Sheets

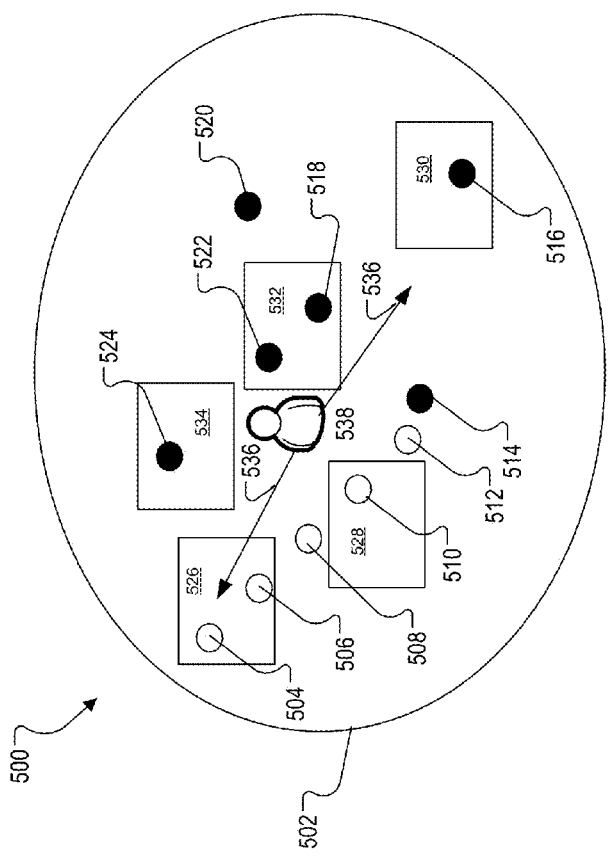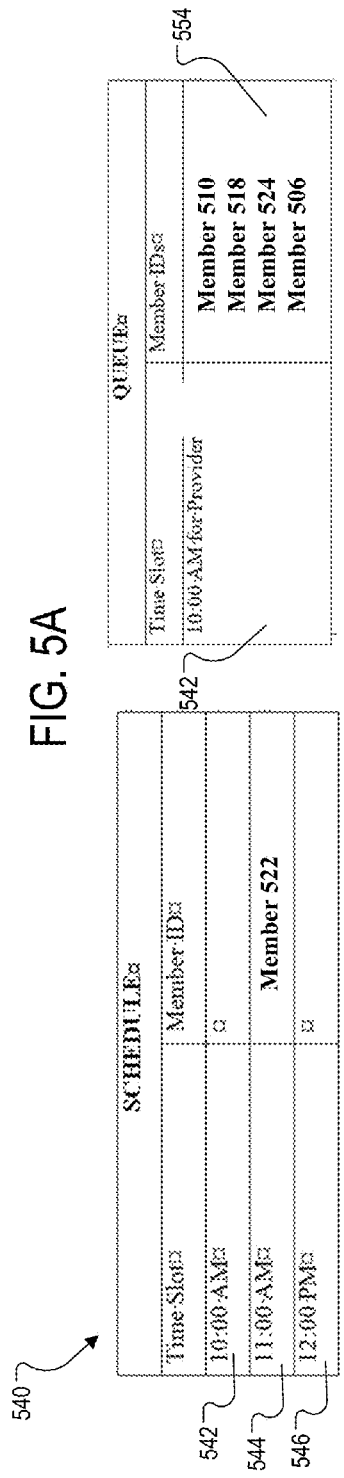

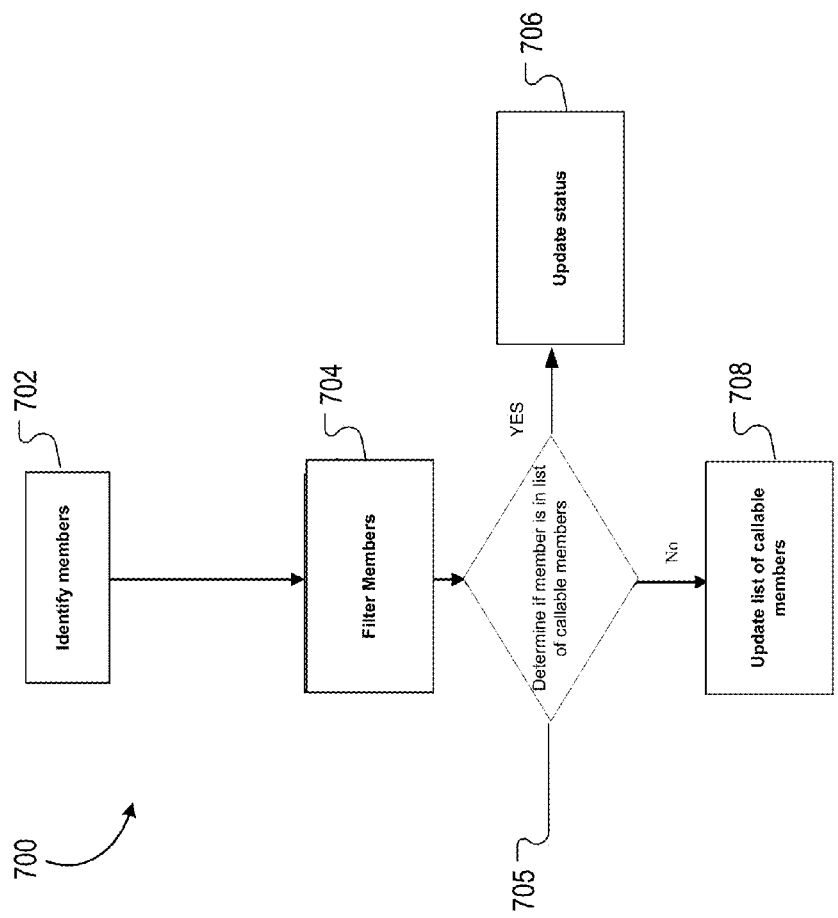

SCHEDULING ASSESSMENTS FOR DETERMINING RISK ADJUSTMENT PAYMENT INFORMATION

BACKGROUND

A health risk assessment (HRA) includes a collection of information from individuals that identifies risk factors, provides individualized feedback, and links the person with at least one intervention to promote health, sustain function and/or prevent disease.

SUMMARY

In general, one innovative aspect of the subject matter described in this specification can be embodied in methods that include the actions of identifying, in a data repository, (i) information indicative of a health care provider who is assigned to a pre-defined calling zone, and (ii) radius information indicative of a radial distance from a starting location that the health care provider will travel to perform a health risk assessment; accessing scheduling information that comprises a plurality of time slots, wherein each time slot corresponds to a time for the health care provider to perform the health risk assessment; selecting, by one or more computer systems, a particular slot from the scheduling information; for the selected slot, applying a geo-dialing algorithm to candidate information that is indicative of one or more members of one or more health plans who are candidates for scheduling in the selected time slot; identifying, based on application of the geo-dialing algorithm, a candidate with a geographic location that is a decreased distance from a geographic location of the health care provider, relative to other distances of other candidates from the health care provider; confirming that geographic location of the identified candidate is within the radial distance; and causing a call to be placed to the identified candidate to promote scheduling of the health risk assessment between the identified candidate and the health care provider at a time that is associated with the selected slot.

Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Implementations of the disclosure can include one or more of the following features. The actions include retrieving a priority call queue, with the priority call queue specifying an order in which the one or more computer systems place calls to candidates in accordance with distances between geographic locations of the candidates and the geographic location of the health care provider; wherein identifying the candidate comprises identifying a candidate ranked first in the priority call queue. The actions include repeating the actions of selecting a slot, applying the geo-dialing algorithm, identifying a candidate and causing a call to be placed until each of the slots in the scheduling information is populated with scheduling information. The actions include determining that a particular candidate is a priority client who is prioritized in scheduling of health risk assessments; retrieving, in a database, a distance offset value that is associated with the particular candidate, with the distance offset value specifying an amount by which a distance between a geographic location of the priority client and the geographic location of the health care provider is decreased to promote scheduling of a health risk assessment for the priority client before scheduling of health risk assessments for other clients; and wherein applying the geo-dialing algorithm to the candidate information comprises: computing distances between geographic locations of the candidates and the geographic location of the health care provider; applying one or more distance offset values to the computed distances; and applying the geo-dialing algorithm to the candidate information and to the computed distances with the applied one or more distance offset values.

The actions include comparing (i) an amount of distance between the geographic location of the identified candidate and the starting location of the health care provider, to (ii) the radial distance; determining whether the amount of distance is less than the radial distance; when the amount of distance is less than the radial distance, causing the call to be placed to the identified candidate to promote scheduling of the selected slot; and when the amount of distance is greater than the radial distance, determining that the identified candidate is ineligible to be seen by the health care provider; and identifying another candidate with another geographic location that is a decreased distance from the geographic location of the health care provider, relative to other distances of other candidates from the health care provider. The actions include receiving acceptance information specifying that the candidate has scheduled the health risk assessment; updating the selected slot with identifying information for the candidate to schedule the health care provider to perform the health risk assessment at a time associated with the selected slot; updating the geographic location of the health care provider to be the geographic location of the candidate who scheduled the appointment; selecting another slot from the scheduling information, with the selected other slot being a next slot in the scheduling information; for the selected other slot, identifying another candidate with a geographic location that is a decreased distance from the updated geographic location of the health care provider, relative to other distances of other candidates from the health care provider; and causing a call to be placed to the identified other candidate.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE FIGURES

FIG. 5A is a conceptual diagram of locations of members and a provider.

FIG. 5B is an example of a schedule.

FIG. 5C is an example of a call queue.

FIG. 7 is a flow chart of a process for identifying callable members.

DETAILED DESCRIPTION

Figure 1:
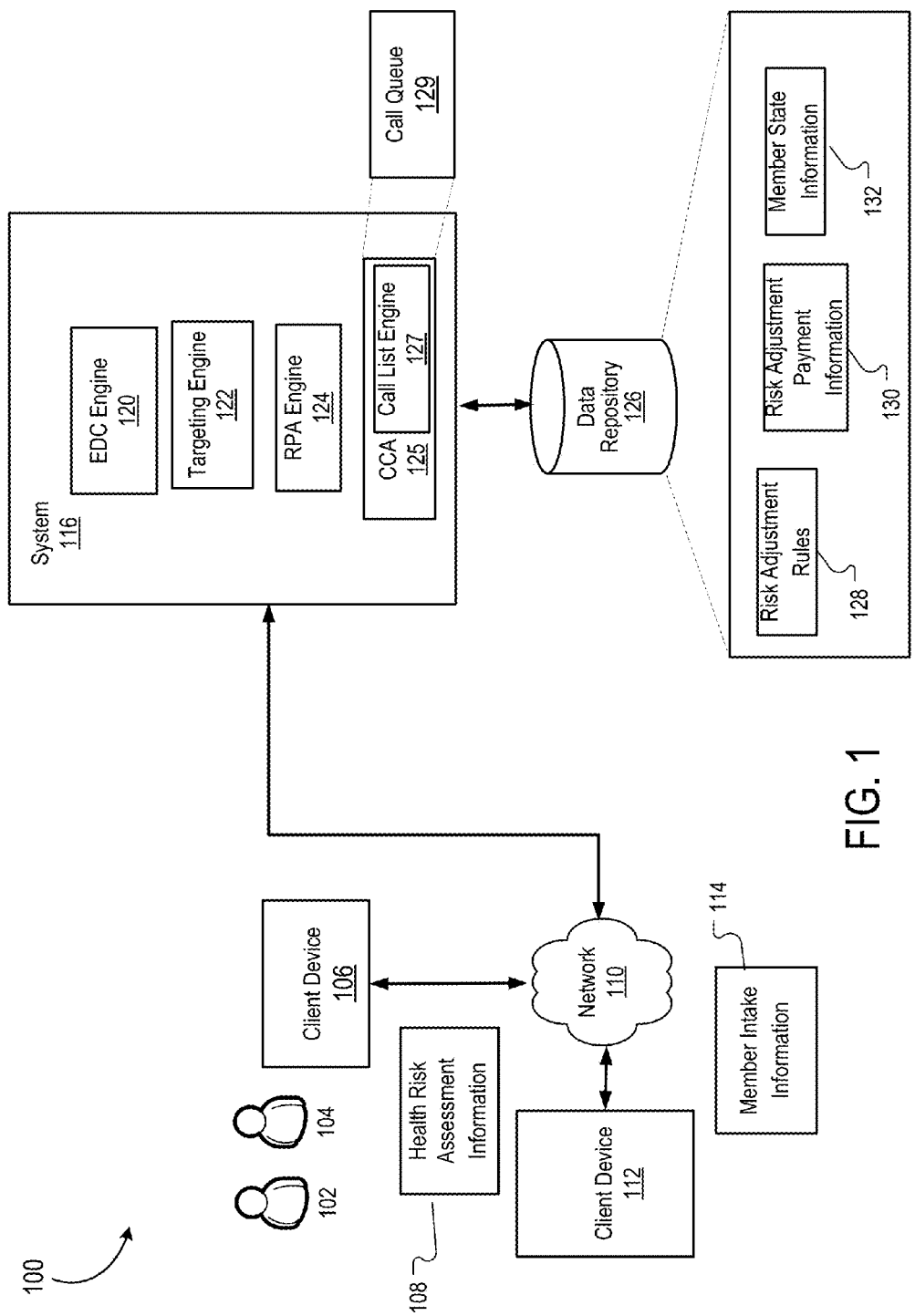
FIG. 1 is a diagram of an environment for determining risk adjustment payment information.

A system consistent with this disclosure determines risk adjustment payment information, including, e.g., information that may be used by health plans (e.g., Medicaid and/or Medicare) in determining risk adjustment payments. In an example, the risk adjustment payment information may include medical codes that are based on medical diagnoses and/or information indicative of medical diagnoses. Generally, risk adjustment includes a process of adjusting health plan payments, health care provider payments and/or premiums to reflect the health status of plan members. In this example, a risk adjustment payment includes an amount by which payments (and/or premiums) are adjusted, e.g., based on an outcome of a risk adjustment process. Risk adjustment includes risk assessment that assesses the relative risk of each person in a group. In this risk adjustment stage, the system implements (and/or facilitates implementation of) a health risk assessment (HRA) to assess the health of a member. Following the risk adjustment stage, the system generates risk adjustment payment information to reflect the determined health risks and that promotes health plan rate adjustment.

In an example, a member is enrolled in a health plan that is part of the Medicare system. In this example, the system identifies the member as being eligible for an appointment with a health care provider (e.g., a Medicare-covered annual wellness visit, a HRA, and so forth) and facilitates the appointment. In another example, the system receives, from a health plan, eligibility information that specifies the member as being eligible for an HRA. The system facilitates the appointment by implementing various processes that promote a health care provider's visitation of the member (e.g., in the member's home) to conduct the HRA. During the appointment, the health care provider furnishes the member with a HRA to collect health risk assessment information (HRA information). Generally, HRA information includes information that is collected during a HRA. The health care provider causes the HRA information to be submitted back to the system. In an example, the system analyses the HRA information to identify new medical diagnoses for the member. In another example, the health care provider diagnoses high risk conditions and/or new medical diagnoses of the member and passes this information back to the system.

Using the new identified medical diagnosis, the system determines risk adjustment payment information for the member, e.g., to promote increase in an amount of benefits that are paid by the health plan for the member. The system determines risk adjustment payment information by identifying additional billing codes that may be used in billing for medical treatments that cover these newly identified medical diagnoses. These billing codes include National Uniform Billing Committee (NUBC) codes, Medicare codes, Medicaid codes, International Classification of Diseases (ICD) codes (e.g., ICD-9 codes and ICD-10 codes), and so forth.

Referring to FIG. 1, an arrangement 100 for using risk adjustment payment information in adjusting premiums/payments and/or coverage based on risk adjustments includes client devices 106, 112, a system 116 for determining risk adjustment payment information, a data repository 126 and network 110. Client device 112 is associated with a health plan (e.g., an insurance company). Client device 112 transmits to system 116 (e.g., via network 110) member intake information 114, e.g., including information indicative of a health history of a member. The member intake information 114 is for a particular member (e.g., member 104). Member intake information 114 may include information indicative of medical claims that have been submitted for a member, medical reports from laboratories on tests that have been conducted on a member, medications that are being taken for a member, medical records of a member, pharmacy prescriptions, name and residence address information, and so forth. Member intake information 114 is compliant with the Health Insurance Portability and Accountability Act (HIPPA).

Client device 106 is used by health care provider 102 (e.g., a nurse practitioner). Health care provider 102 uses client device 106 to view an electronic HRA to ask member 104 questions about the health status of the member 104. As member 104 provides health care provider 102 answers to the questions included in the HRA, health care provider 102 inputs the answers to the questions into client device 106, as at least part of the health risk assessment information 108. Client device 106 transmits to system 116 health risk assessment information 108 that is stored in data repository 126. In an example, health care provider 102 uses the answers to the HRA to identify new medical diagnoses and uses client device 106 to submit these new medical diagnoses to system 116.

System 116 includes various engines, e.g., targeting engine 122, electronic data capture (EDC) engine 120, and resource planning and analysis (RPA) engine 124. System 116 executes a call center application 125 that includes a call list engine 127. In the illustrative example of FIG. 1, EDC engine 120 of system 116 receives the health risk assessment information 108 and causes the health risk assessment information 108 to be stored in the data repository 126.

Targeting engine 122 determines high risk members who should have an HRA (and/or for another type of appointment such as a Medicare-covered annual wellness visit). Targeting engine 122 determines member risk at least partly based on application of targeting rules to member intake information 114. Generally, a targeting rule includes one or more instructions for analyzing information. Based on application of the targeting rules to member intake information 114 for a particular member, targeting engine 122 generates a risk score for the particular member. When the risk score exceeds a threshold score, targeting engine 122 determines that the member is eligible for the HRA.

The targeting rules include instructions to analyze member intake information 114 (e.g., claims data included in member intake information 114) and to determine when the member's last annual examination occurred. The targeting rules include instructions that when the last annual examination occurred more than a year ago to assign the member a risk score of seventy-five. In this example, the threshold score has a value of fifty. Targeting engine 122 determines that the risk score exceeds the threshold score and that the member is eligible for the HRA. Targeting is determined (e.g., by targeting engine 122) by a programmatic examination of the prior medical claims, prior prescription claims, and data available from any lab results that have occurred within a certain period of time. Targeting engine 122 executes a series of rules that examine the data components aggregated (e.g., member intake data) within these data structures and determines a risk level for the member based on the rules embedded within the risk scoring algorithm (and contents of the member intake information). For example, a member whose claim history indicates they are taking insulin would have a high risk score for diabetes. In an example, the targeting rules scan the member intake information to detect an absence (or a presence) of a keyword specifying a predefined state or criteria (e.g., completion of the health risk assessment). The targeting rule is associated with a numeric score, such that detection of the predefined state or criteria assigns the numeric score to be the risk score for the member. In this example, based on the detected absence, the targeting rules assign the member a risk score that specifies that the member is due for a health risk assessment. In this example, targeting engine 122 receives member intake information only for eligible members, e.g., members that have been identified by a health plan as being eligible for an HRA.

In still another example, system 116 makes a determination of eligibility. In this example, system 116 analyses member intake information to determine whether the member is enrolled in a qualified health plan that entitles the member to the HRA and/or to determine that the member is not deceased and has not reached a threshold limit for received benefits. In this example, system 116 determines that when the risk score exceeds the threshold score and when the member is eligible that the member may be scheduled for an HRA.

Following determination that the member is targeted for an HRA, the RPA engine 124 selects members to receive invitations to schedule HRAs. The invitations are electronic messages, e.g., sent in the form of e-mails. Alternatively, the invitations are mailed to residences of members. Other techniques for sending the invitations can be used. RPA engine 124 may notify users of system 116 of the selected members and the notified users generate mailings to send to the selected members.

In an example, RPA engine 124 selects members based on the supply (and/or density) of health care providers (e.g., health care providers who are registered or otherwise associated with system 116) in a geographic location in which the member is located. As discussed above, the member intake information 114 includes information identifying a geographic location of a member (e.g., information specifying a zip code of the member). In this example, data repository 126 stores information indicative of health care providers who are participating in system 116, including, e.g., information identifying a geographic location of the health care providers. RPA engine 124 analyses (e.g., compares) the information identifying geographic locations of the health care providers and the information identifying the geographic location of the members to select members to be notified of HRAs in a particular geographic location. For example, RPA engine 124 may assess that a predefined notification number (e.g., ten) of members in a particular geographic location are notified of the opportunity for a HRA for each health care provider who is also located in that geographic location. In this example, RPA engine 124 identifies a number of health care providers in a particular geographic location and then multiples the identified number of health care providers by the predefined notification number to determine the number of members to select for invitation in a particular geographic location.

In another example, RPA engine 124 also selects member based on various other factors, including, e.g., various calendar seasons. For example, members may more positively respond (e.g., higher response rate) in certain seasons than in other seasons. For example, members may more positively respond to the invitations to schedule the HRA in the spring rather than in the winter. In this example, RPA engine 124 may be configured to adjust a number of selected members by an adjustment value, e.g., based on the current season. For example, using the above-described techniques, RPA engine 124 may determine a number of members to select. In this example, an adjustment value is associated with particular seasons. If RPA engine 124 determines that a current season matches one of the particular seasons that are associated with the adjustment values, RPA engine 124 adjusts the number of selected members by the adjustment value (e.g., a 25% increase in a number of selected members, a 25% decrease in a number of selected members, and so forth).

In this another example, RPA engine 124 selects members to be notified of the opportunity to schedule HRAs based on availability of the health care providers in a particular geographic location, e.g., in addition to or rather than being based on a number of health care providers in the particular geographic location. As described in further detail below, data repository 126 maintains schedules for the health care providers who are registered with system 116. These schedules include appointment slots, with an appointment slot being associated with a particular time. As members schedule appointments, system 116 populates the appointment slots to schedule the appointment. In this example, RPA engine 124 selects members based on a number of available appointment slots for a particular geographic location. For example, RPA engine 124 may assess that a predefined available appointment slot notification number (e.g., ten) of members in a particular geographic location are notified of the opportunity for a HRA for each available appointment slot of a health care provider who is also located in that geographic location. RPA engine 124 identifies a number of available appointment slots for health care providers in a particular geographic location and then multiples the identified number of available appointment slots by the predefined available appointment slot notification number to determine the number of members to select for invitation in a particular geographic location.

In this example, a member (e.g., member 104) accepts the invitation, e.g., by responding to an email and specifying acceptance, by mailing back a postcard, and so forth. System 116 receives information specifying that member 104 accepts the invitation and saves this received information in data repository 126.

For a member who is targeted to receive a HRA, who has been selected by the RPA engine 124 and who accepts the invitation, system 116 executes CCA 125 to promote scheduling of the HRA. As described in further detail below, CCA 125 includes call list engine 127 that executes various real-time processes to identify an order (e.g., a priority) in which selected members are called to schedule HRAs. In this example, call list engine 127 generates call queue 129 specifies an order in which members are called to schedule a HRA (e.g., for a particular time slot of a particular provider). In this example, information identifying member 104 is included in call queue 129.

In the example of FIG. 1, a call center agent (not shown) places a call to member 104 and successfully schedules a HRA with provider 102, e.g., in a home of member 104. The call center agent can be a human or a machine, e.g., "robo" calling system. In response, system 116 updates a schedule of health care provider 102 by populating an appointment slot (e.g., in a schedule of provider 102) with information for member 104 (e.g., an address of member 104 and/or a telephone number of member 104).

At the specified time and date, health care provider 102 performs a HRA on member 104. In this example, health care provider 102 uses client device 106 to view and to access an electronic HRA. As previously described, health care provider 102 inputs, into client device 106, health risk assessment information 108 that is transmitted to system 116. In this example, health care provider 102 may also identify additional medical diagnoses (e.g., based on results of the HRA) and may send information indicative of these additional medical diagnoses to system 116, e.g., for storage.

In a variation, system 116 applies risk adjustment rules 128 (which are stored in data repository 126) to health risk assessment information 108 to identify a medical diagnosis for member 104. In this example, identified medical diagnosis is a new medical diagnosis, which was previously unidentified in member intake information 114. Generally, a risk adjustment rule includes a mapping of diagnosis information to an item of medical information (e.g., a keyword that is included in medical record). Generally, diagnosis information includes information indicative of a medical diagnosis. An example risk adjustment rule is provided in the below Table 1.

TABLE 1

| Diagnosis information | Medical information |
| --- | --- |
| Throat ulcer | Pain in lower throat |

As shown in the above Table 1, medical information of "pain in lower throat" is associated with a diagnosis of "throat ulcer." In this example, risk adjustment rules 128 include the risk adjustment rule shown in the above Table 1. System 116 analyses health risk assessment information 108 and detects the words "pain in lower throat" in health risk assessment information 108. Based on execution of risk adjustment rules 128, system 116 determines that the words "pain in lower throat" are associated with (e.g., mapped to) a diagnosis of "throat ulcer."

System 116 also accesses in data repository 126 medical code information (not shown). An item of medical code information specifies a medical code (e.g., a billing code) that classifies a particular medical diagnosis or inpatient procedure, as shown in the below Table 2.

TABLE 2

| Medical Code | Diagnosis information |
| --- | --- |
| ICD9-ABC | Throat ulcer |

As shown in the above Table 2, diagnosis information of "throat ulcer" is associated with an "ICD9-ABC" medical code. Using the accessed medical code information and the identified diagnosis, system 116 determines risk adjustment payment information 130, e.g., based on identification of a new diagnosis in health risk assessment information 108. In an example, risk adjustment payment information 130 may differ from a risk adjustment payment, which is determined by a health plan. Risk adjustment payment information includes a medical code or other information that assists a health plan in adjusting payments for a member. Risk adjustment payment information 130 includes the "ICD9-ABC" medical code that is associated with a diagnosis of throat ulcer. System 116 transmits to a system associated with an insurance company and/or a health plan (e.g., client device 112) risk adjustment payment information 130 that includes medical code information that is indicative of the determined medical code, e.g., to enable the insurance company to use the new medical code in billing (e.g., in billing Medicare or Medicaid) for treatment of the new diagnosis and to enable the member to receive treatment for this new diagnosis. Data repository also stores member state information 132, including, e.g., information indicative of a state of a member as the member progresses through various states of scheduling a HRA, as described in further detail below.

System 116 also measures a potential return on investment (ROI) of the newly identified diagnosis. System 116 calculates the ROI by examining the current reimbursement for the member as identified by the health plan and prior RAPs (requests for anticipated payment) and file submissions to CMS (Center for Medicare & Medicaid Services) and determining how much the payment for the member would change if the diagnosis were included in future RAPs submissions for the member in question.

Figure 2:
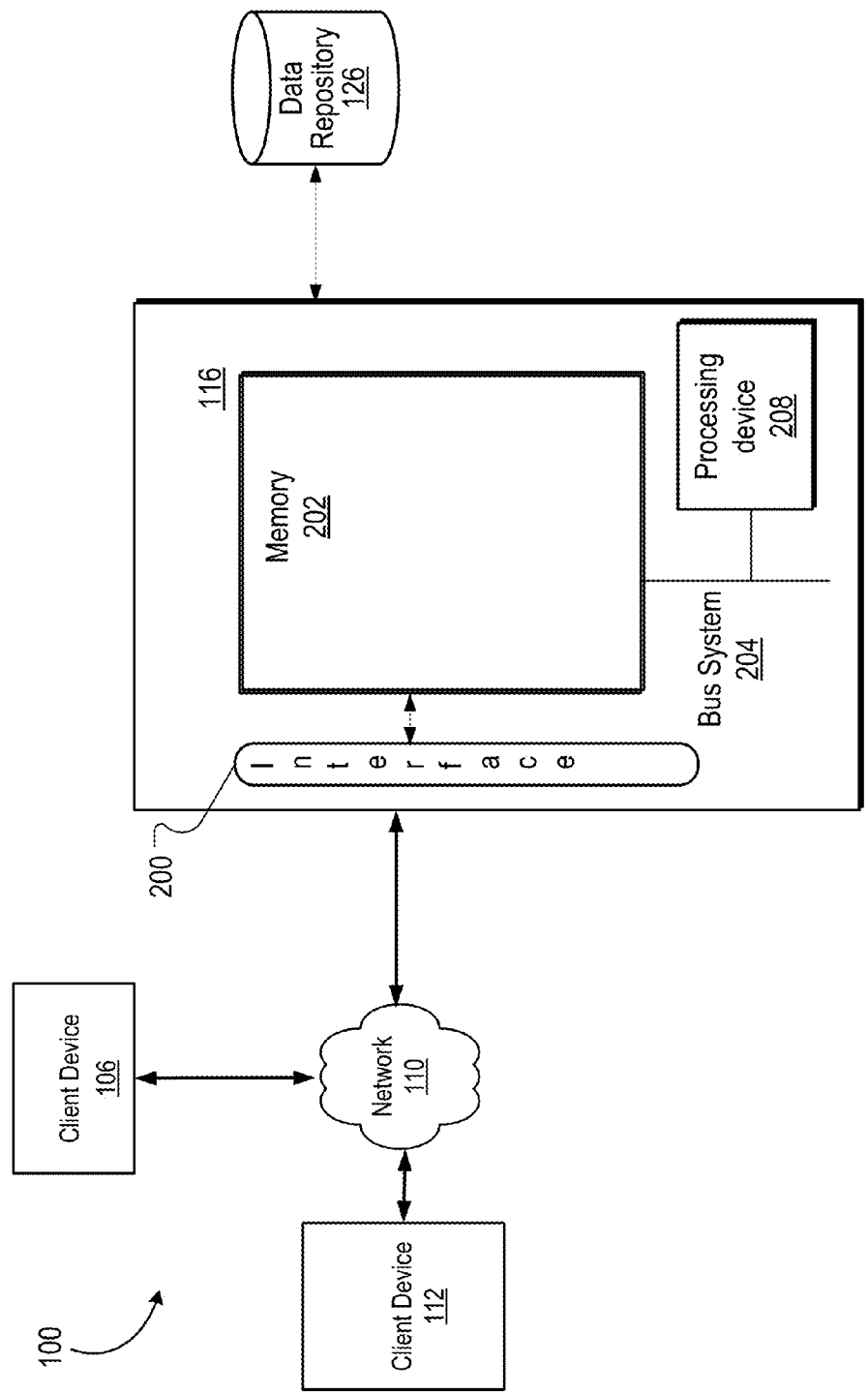
FIG. 2 is a block diagram of components of the environment for determining risk adjustment payment information.

Referring now to FIG. 2, hardware components of the various systems included in arrangement 100 are shown. In FIG. 2, each of client devices 106, 112 can be any sort of computing device capable of taking input from a user and communicating over network 110 with system 116, other client devices, and/or other systems. For example, each of client devices 106, 112 can be a mobile device, a desktop computer, a laptop, a cell phone, a smartphone, a tablet, a personal digital assistant (PDA), a server, an embedding computing system, and so forth.

System 116 can be any of a variety of computing devices capable of receiving data, such as a server, a distributed computing system, a desktop computer, a laptop, a cell phone, a rack-mounted server, and so forth. System 116 may be a single server or a group of servers that are at the same location or at different locations.

The illustrated system 116 can receive data from one or more of client devices 106, 112 via input/output (I/O) interface 200. I/O interface 200 can be any type of interface capable of receiving data over a network, such as an Ethernet interface, a wireless networking interface, a fiber-optic networking interface, a modem, and so forth. System 116 also includes a processing device 208 and memory 202. A bus system 204, including, for example, a data bus and a motherboard, can be used to establish and to control data communication between the components of system 116.

The illustrated processing device 208 may include one or more microprocessors. Generally, processing device 208 may include any appropriate processor and/or logic that is capable of receiving and storing data, and of communicating over a network (not shown). Memory 202 can include a hard drive and a random access memory storage device, such as a dynamic random access memory, or other types of non-transitory machine-readable storage devices. Memory 202 stores computer programs (not shown) that are executable by processing device 208 to perform the techniques described herein.

Figure 3:
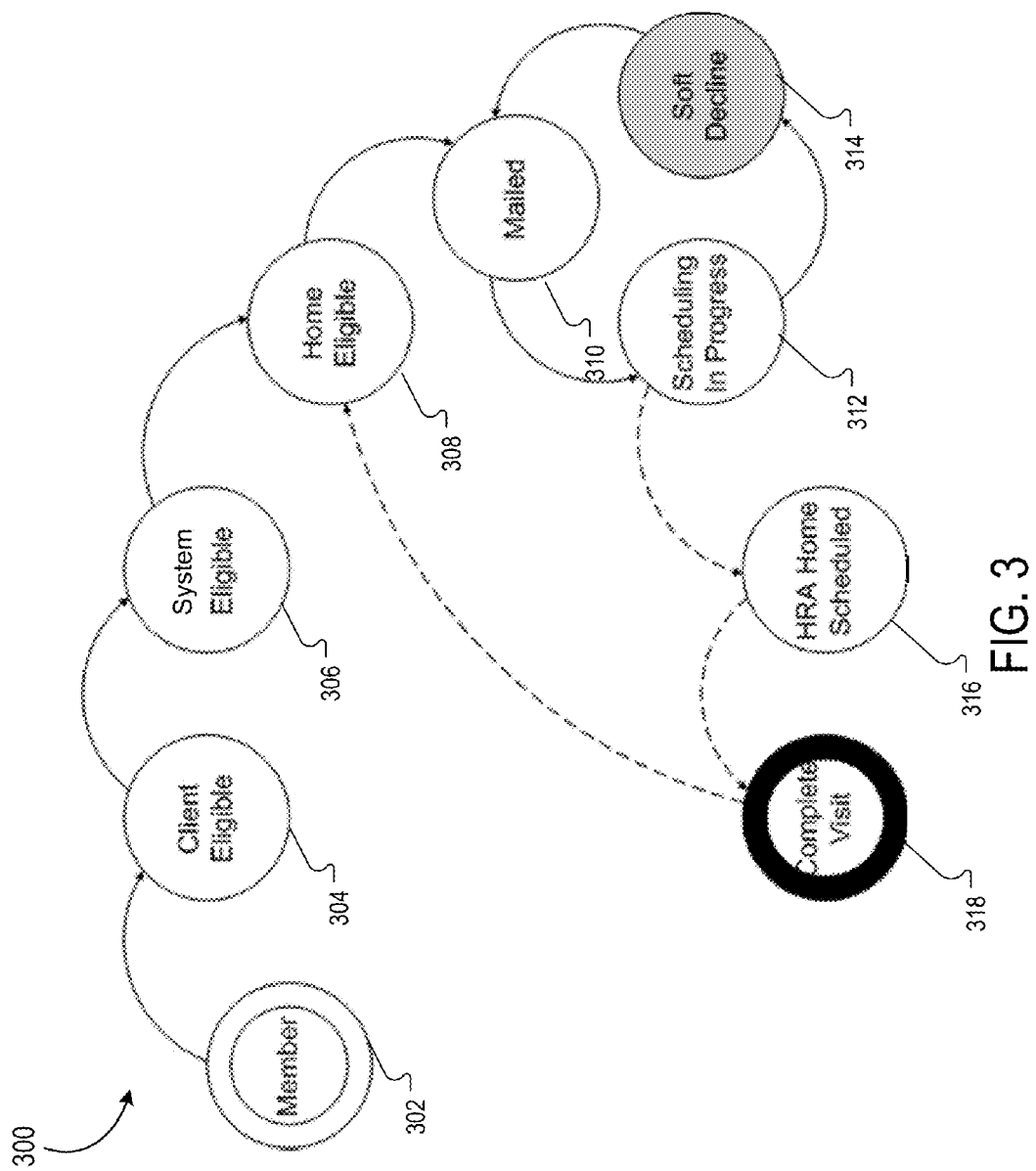
FIG. 3 is a conceptual diagram of types of information included in a database record for a member.

Referring now to FIG. 3, diagram 300 includes the various states of scheduling a HRA. At member state 302, system 116 receives member intake information, e.g., from a health plan. At member state 302, member state information for the member is updated to include information specifying identifying member information, e.g., a name or a unique member identifier, and also information included in member intake information.

At client eligibility state 304, system 116 receives eligibility information, e.g., from a health plan. A health plan may determine that a member is eligible for an HRA when the plan provides for an HRA. In a variation, system determines whether the member is enrolled in a qualified health plan that allows for HRAs or otherwise allows for annual visits. If the member is not enrolled in a qualified health, system 116 specifies that the member is not eligible for a HRA and updates the member state information to reflect this ineligibility. If the member is client eligible, system 116 updates member state information to reflect this eligibility.

At system eligibility state 306 (which is implemented by targeting engine 122), system 116 determines whether the member is not deceased and has not reached a threshold amount of received benefits. If the member does not satisfy these system eligibility criteria, system 116 specifies that the member is not selected eligible for a HRA and updates the member state information to reflect this. If the member does satisfy these system eligibility criteria, system 116 updates the member state information to reflect this eligibility and system 116 determines whether the member is home eligible, e.g., meaning whether the member is targeted for an in-home HRA.

At this home eligibility state 308, system 116 determines whether the user is eligible for an in-home HRA, e.g., based on whether the targeting rules specify that the member is a high risk member, based on benefits of the member's health plan, based on date of last HRA, and so forth. If the member is eligible for an in-home HRA, member state information for the member is updated to reflect this eligibility.

At mailing state 310, member state information is updated with information specifying that a member is notified of the opportunity to schedule a HRA. At scheduling in progress state 312, member state information is updated to reflect that system 116 is attempting to schedule a HRA with the member. Member state information is also updated to reflect soft decline state 314, e.g., a member has declined the HRA but has asked to be contacted later. Member state information is also updated (e.g., by system 116) to include HRA home scheduled state 316, e.g., information specifying that a HRA is scheduled. Member state information is updated to include complete visit state 318, e.g., information specifying completion of a HRA. At each of the states 302-318, member state information is updated by system 116 to reflect a state (e.g., status) of a member.

Figure 4A:
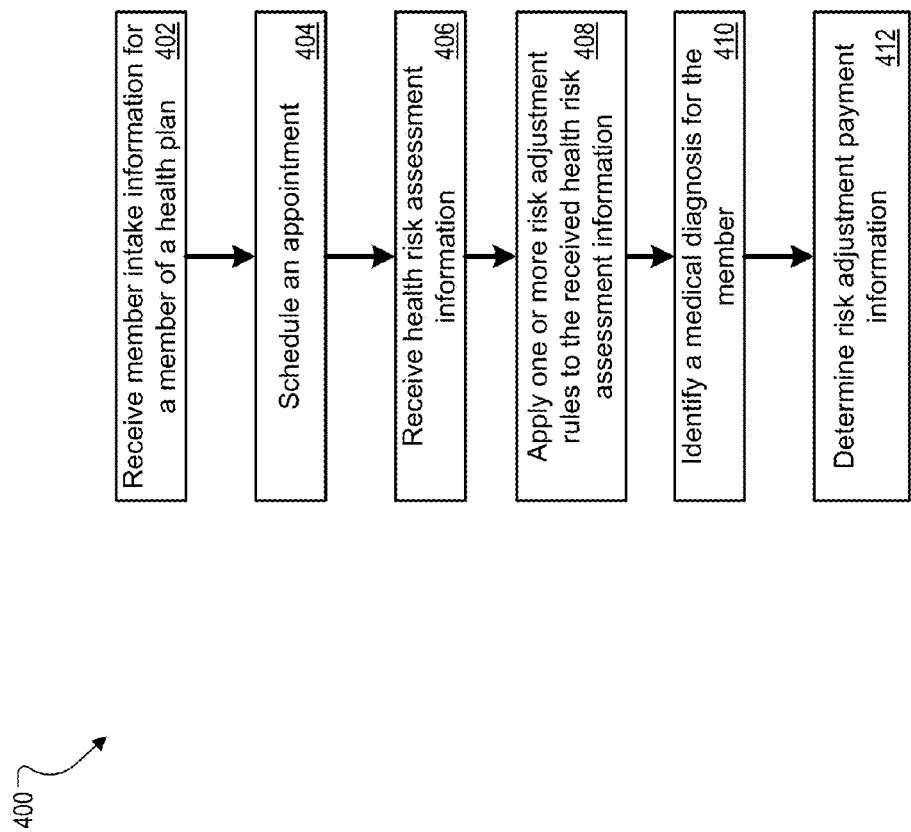
FIGS. 4A, 4B are flow charts of processes for determining risk adjustment payment information.

Referring to FIG. 4A, system 116 implements process 400 in determining risk adjustment payment information. In operation, system receives (402) member intake information for a member of a health plan. System 116 determines (not shown) that the member is eligible for a HRA and selects the member to be notified of the opportunity to schedule the HRA. System 116 receives information specifying that the member accepts the invitation to schedule the HRA. In response, system 116 schedules (404) an appointment between a health care provider and the member for the health care provider to perform a health risk assessment, as described in further detail below. As described in further detail below, once the member accepts the invitation and indicates that the member wants to schedule a HRA, system 116 updates a data record of the member (e.g., a profile of the member or member state information) as being a callable member. The data record of the member also includes a geo-code for a residence of the member or other information identifying a geographic location of the member. In an example, system 116 performs scheduling for various providers. When system 116 does scheduling for a provider (e.g., to schedule available time slots for a provider), system 116 queries data repository 126 for a list of callable members and/or for a list of callable members who are located in proximity to the provider (e.g., with a specified distance from the provider). As described in further detail below, system 116 executes a geo-dialing algorithm to schedule the available time slots in a manner than decreases an amount of travel by the service provider between various locations in which the HRAs are conducted.

System 116 receives (406), from a client device used by the health care provider, health risk assessment information that is collected during the health risk assessment. System 116 applies (408) one or more risk adjustment rules to the received health risk assessment information. System 116 identifies (410) a medical diagnosis for the member, with the identified medical diagnosis being unidentified in the member intake information. System 116 determines (412), based on the identified medical diagnosis, risk adjustment payment information that promotes an adjustment by a health plan in health payments, e.g., to increase an amount of benefits that are paid by the health plan for the member, relative to another amount of benefits that were paid prior to the health risk assessment. The risk adjustment payment information includes an additional billing code that may be used in billing for health services that are provided to the member.

Figure 4B:
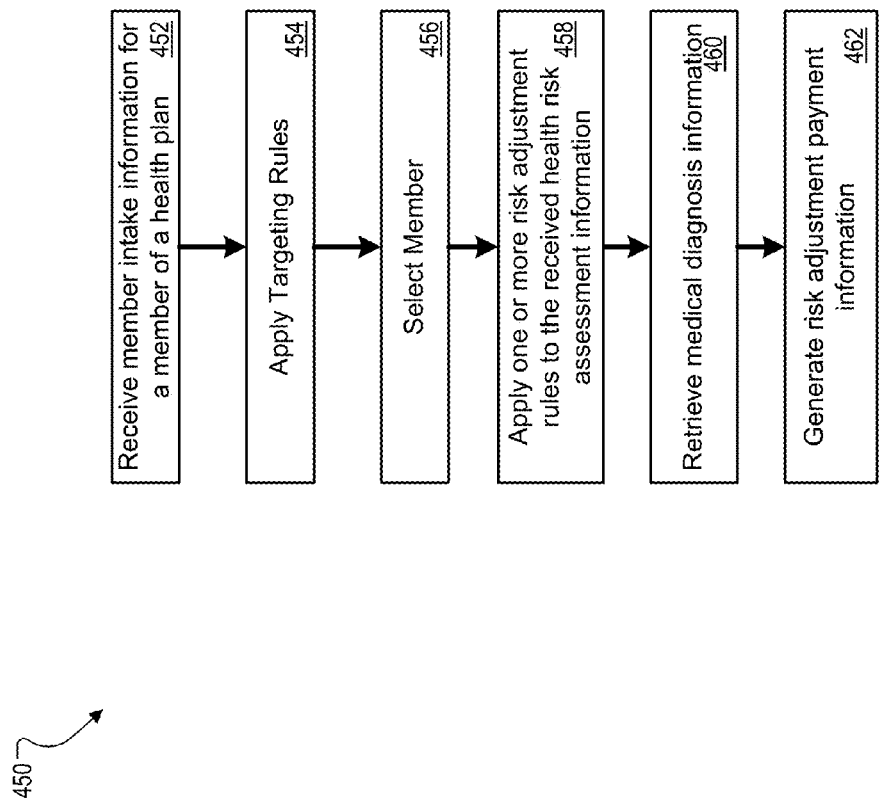

Referring to FIG. 4B, system 116 implements process 450 in generating risk adjustment payment information. In operation, system 116 receives (452) member intake information for a member of a health plan including a first set of medical diagnoses. System 116 applies (454) one or more targeting rules to the received member intake information. System 116 determines (not shown), based on application of the one or more targeting rules, a risk score for the member. System 116 selects (e.g., identifies) (456), at least partly based on the risk score, the member for participation in a health risk assessment. System 116 receives, from a client device used by a health care provider, health risk assessment information that is collected during the health risk assessment that is conducted by the health care provider. System 116 retrieves (460) medical diagnosis information that is based on an analysis of the health risk assessment information, with the medical diagnosis information being indicative of one or more medical diagnoses for the member, with the one or more medical diagnoses being different from the medical diagnoses in the first set included in the member intake information. System 116 retrieves the medical diagnosis information from data repository 126. A health care provider identifies the medical diagnoses and uses a client device to transmit the identified medical diagnoses to system 116 for storage in data repository 126. System 116 generates (462) risk adjustment payment information, e.g., identifying billing codes that are relevance to the new medical diagnoses. System 116 transmits (e.g., to a health plan) the risk adjustment payment information that is at least partly based on the medical diagnosis information, with the risk adjustment payment information comprising information that promotes determination of a risk adjustment payment.

The scheduling of appointments is based on provider availability and based on an assignment of a health care provider to a particular geographic zone. Generally, a geographic zone includes a specified geographic area.

Referring to FIG. 5A, diagram 500 shows a boundary 502 that is representative of the geographic boundary of a specified geographic location (e.g., a state). In this example, member visual representations 504, 506, 508, 510, 512, 514, 516, 518, 520, and 524 represent members to be scheduled for HRAs, e.g., callable members, a health care provider is represented by visual representation 538 and geographic zones, e.g., 526, 528, 530, 532, and 534 circumscribe several of the member visual representations, and are zones assigned to health care provider 538 by system 116.

Generally, a callable member includes a member who is a candidate to be called to schedule a HRA. Is this example, locations of each of member visual representations 504, 506, 508, 510, 512, 514, 516, 518, 520, and 524 are positioned in boundary 502 in accordance with actual geographic locations of the members (represented by member visual representations 504, 506, 508, 510, 512, 514, 516, 518, 520, and 524). For example, member visual representation 504 specifies a geographic location of a residence of a member (represented by member visual representation 504) in the state (represented by boundary 502). Member visual representation 522 represents a member who is already scheduled for a HRA with health care provider 538. The location of health care provider 538 in boundary 502 reflects a geographic location (e.g., a starting location) of the health care provider 538 in the state. Members represented by member visual representations 504, 506, 508, 510, 512 are members of a health plan ("health plan A"). Members represented by member visual representations 514, 516, 518, 250, 522, 524 are members of another health plan ("health plan B").

Health care provider 538 provides medical services to members in the state according to the system 116 assigned geographic zones 526, 528, 530, 532, 534. Generally, a geographic zone specifies an area or a region in which system 116 has specified that a health care provider may perform HRAs, e.g., to promote an even distributions of health care providers across a geographic region and/or state.

System 116 also assigns radial distance 536 to health care provider 538, e.g., to reduce travel time between HRAs and to promote efficient travels between locations for performance of HRAs. With the system 116 assigned radial distances, health care provider 538 generally will not travel to a member that is further away than radial distance 536, for the health care provider even if the member is otherwise in an assigned zone of health care provider 538.

Referring now to FIG. 5B, system 116 retrieves, from data repository 126, schedule 540 for health care provider 538. Schedule 540 includes time slots 542, 544, 546. Time slot 544 is already scheduled for member 522. Time slots 542, 546 are empty and are available to be scheduled. To populate (i.e., schedule) time slot 542, system 116 retrieves a list of callable members for health care provider 538. In this example, the callable members include members who are geographically located in a same region (e.g., state) as health care provider 538 and who have accepted the invitation to schedule the HRA. System 116 filters the callable members list by excluding those members who are located outside of zones 526, 528, 530, 532, 534. The excluded members include the members who are represented by member visualization 508, 512, 514, 520. System 116 can further filter the callable members by removing those members who are located at a distance that is beyond radial distance 536, e.g., even if those members are otherwise within a zone of provider 538. In this example, system 116 further removes members represented by member visual representations 504, 516, 512, as those members are located beyond radial distance 536. For the remaining callable members, system 116 determines health plans of those callable members and determines whether health care provider 538 is credentialed with those various plans. For plans for which provider 538 is not credentialed, members associated with those plans are also removed from the list of callable members for provider 538. In the example of FIG. 5A, provider 538 is credentialed with both health plans A and B.

Referring to FIG. 5C, system 116 generates queue 554 for slot 542 to populate time slot 542 in schedule 540. Queue 554 specifies an order in which callable members are called to fill slot 542. In this example, slot 542 is the first appointment of the day for provider 538. System 116 retrieves, from data repository 126, information indicative of a starting geographic location of provider 538. The starting location may include a location of a residence of provider 538, a location of an office of a provider 538, and so forth. The information indicative of the starting geographic location includes a geocode of the starting location. System 116 also retrieves, from data repository 126, geocodes of each of the call members (e.g., the members who remain on the filtered list of call members). Using the geocodes, system 116 executes a geo-dialing algorithm that calculates a distance (e.g., a straight-line distance) between provider 538 and each of the callable members. System 116 determines that the member associated with member visual representation 510 is the closest to the starting location of provider 538 (e.g., the distance between provider 538 and the member associated with member visual representation 510 is the shortest, relative to distances between provider 538 and other callable members). System 116 places information indicative of the member associated with member visual representation 510 first in the queue 554, e.g., to specify that a call center agent calls this member 510 first in an attempt to schedule slot 542.

System 116 determines that the member associated with member visual representation 518 is the second closest to the starting location of provider 538 (e.g., the distance between provider 538 and the member associated with member visual representation 518 is the second shortest). System 116 places information indicative of the member associated with member visual representation 518 second in the queue, e.g., to specify that a call center agent calls this member second in an attempt to schedule slot 542—when the member to be called first does not answer or refuses to schedule an appointment. System 116 determines that the member associated with member visual representation 524 is the third closest to the starting location of provider 538 (e.g., the distance between provider 538 and the member associated with member visual representation 524 is the third shortest). System 116 places information indicative of the member associated with member visual representation 524 third in the queue, e.g., to specify that a call center agent calls (and/or that system 116 causes a call to be placed to) this member third in an attempt to schedule slot 542. System 116 determines that the member associated with member visual representation 506 is the farthest away from the starting location of provider 538 (e.g., the distance between provider 538 and the member associated with member visual representation 506 is the farthest, e.g., relative to distanced between provider 538 and other callable members). System 116 places information indicative of the member associated with member visual representation 506 last in the queue, e.g., to specify that a call center agent calls this member last in an attempt to schedule slot 542, when the other members refuse to answer or decline scheduling an appointment.

The first member from queue 554 to agree to schedule an appointment is scheduled in slot 542. In the example of FIG. 5B, slot 544 is already scheduled. In a variation of FIG. 5B, slot 544 is not scheduled. In this variation, system 116 repeats the above-described actions to schedule slot 544 using a geographic location at which the HRA scheduled for slot 542 takes place as the starting location.

System 116 also repeats the above-described actions to populate slot 546, using the location of the member represented by member visual representation 522 as the starting location and excluding any members who are located more than the radial distance 536 from the original starting location of provider 538.

Figure 6A:
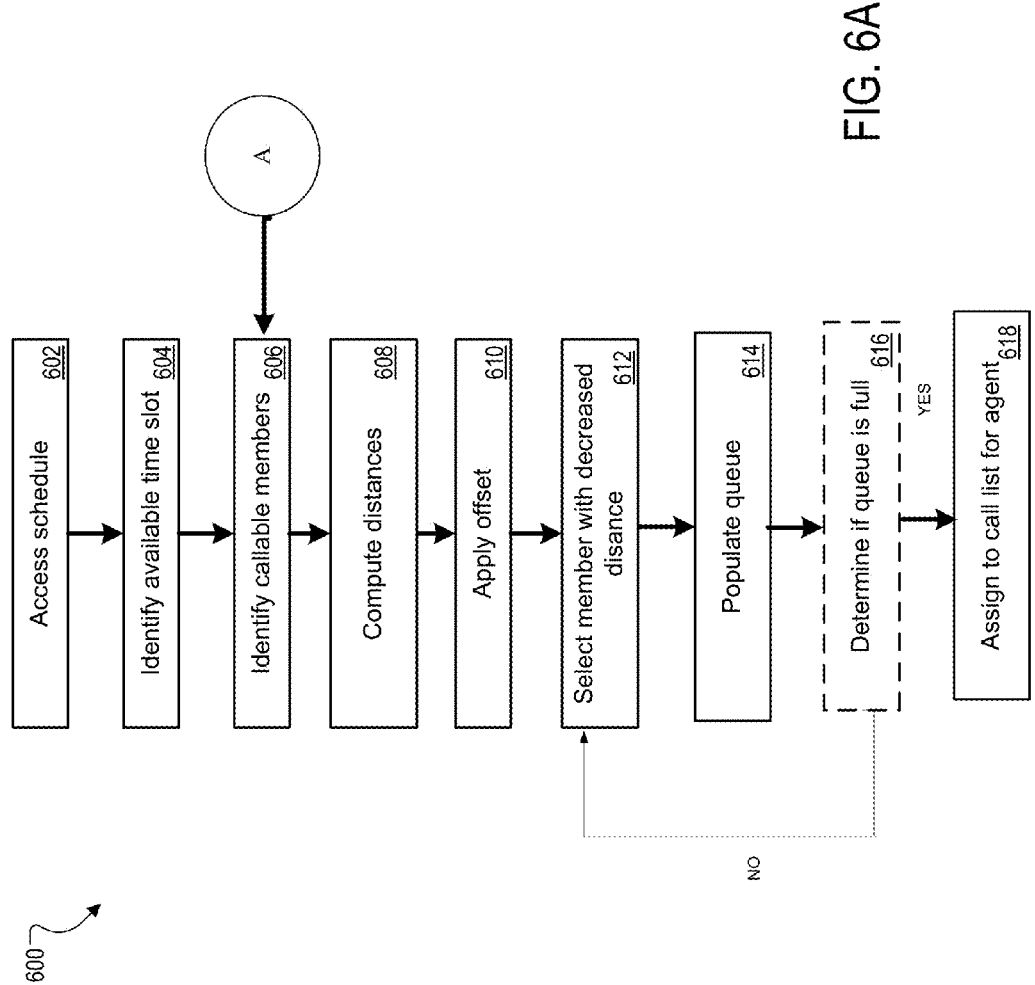
FIGS. 6A-6B, 9 and 10 are flow charts of processes for generating call queues.

Referring to FIG. 6A, system 116 implements process 600 in generating a call queue. In operation, system 116 accesses (602) a schedule of a provider. System 116 identifies (604) an available time slot in the schedule. For the identified time slot, system 116 identifies (606) callable members. System 116 identifies callable members by identifying members who are located in a same geographic region (e.g., city, state or county) as the provider. The identification of callable members is described in further detail below. For one or more of the identified callable members, system 116 uses geocodes of the members and geocode of the provider (e.g., a geocode of a starting location of the provider, a geocode of a location of a scheduled appointment of the provider, and so forth) to compute (608) distances between geographic locations of the members and a geographic location of the provider. System 116 applies (610) an offset (if any) to the computed distances. Offsets are described in further detail below. System 116 selects (612) information indicative of a member with a decreased amount of distance to a geographic location of the provider, e.g., relative to other amounts of distances of other members to the provider. System 116 populates (614) a call queue with information indicative of the selected member. System 116 populates the call queue such that other members with decreased distances are ranked above the selected member and still other members with increased distances are ranked below the selected member.

System 116 determines (616) if the call queue is full. System 116 specifies a predefined number of slots in the call queue. If the call queue is not full, system 116 repeats actions 612, 614, 616, e.g., until the call queue is full. If the call queue is full, system 116 assigns (618) the call queue (for the particular time slot for the particular provider) to a call list for a call center agent. A call list includes an aggregation of various call queues for various time slots to be filled. The call list may include call queues for various different providers. The order in which call queues are arranged within a call list may be based on appointment date, e.g., with call queues for more imminent time slots being ranked above other call queues for time slots that are occurring at a later point in time.

Figure 6B:
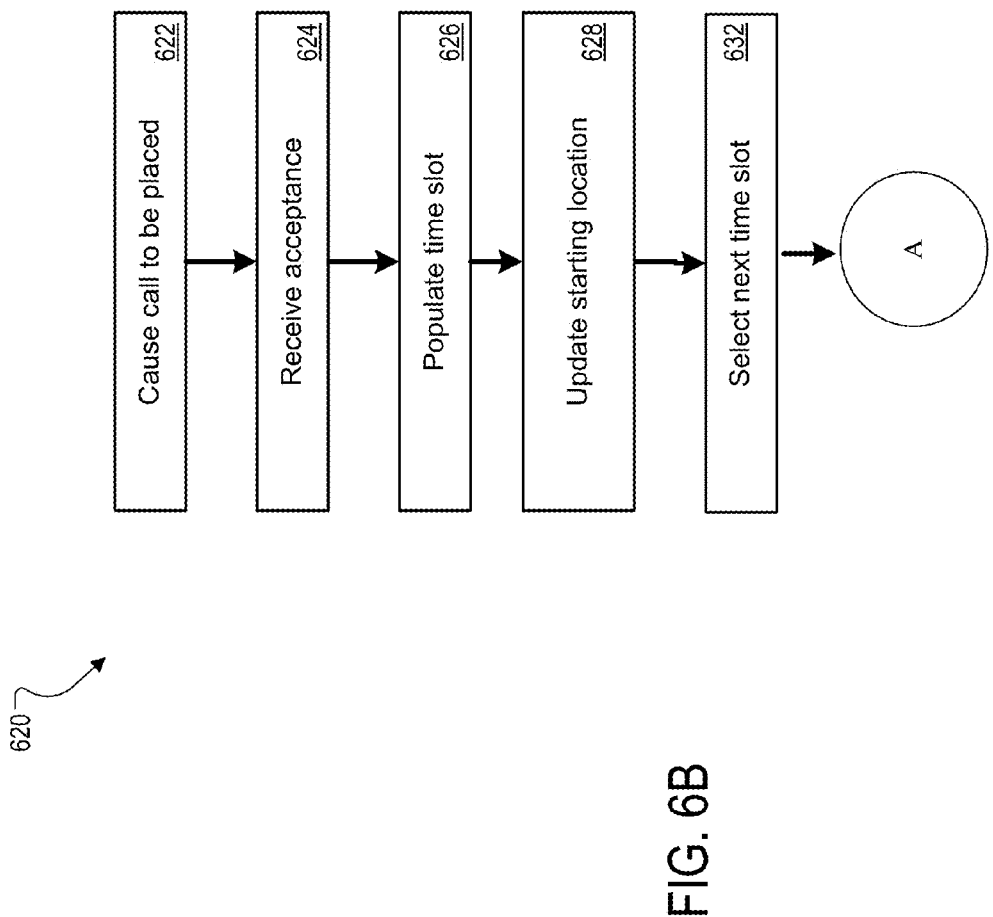

Referring to FIG. 6B, system 116 implements process 620 in scheduling time slots. In operation, system 116 causes (622) a call to be placed to a member who is specified in a queue. In this example, system 116 includes automatic dialing software to cause a call to be placed to a member (e.g., at a telephone number associated with the member). System 116 receives (624) information indicative of acceptance to schedule the HRA. In this example, the call center agent transmits to system 116 information specifying which member has scheduled an appointment for which time slot. System 116 populates (626) the time slot, for which the member accepts the HRA, with information identifying the member, e.g., information specifying a name of the member, a geographic location of the member, and so forth.

System 116 also updates (638) a starting location of the provider to be the geographic location of the scheduled time slot, e.g., that was scheduled via action 626. System 116 selects a next, available time slot in the schedule of the service provider and repeats actions 406, 408, 410, 412 (FIG. 6A) using the updated starting location (the geographic location of the scheduled time slot that was scheduled via action 626).

In an example, call list engine 127 implements process 700 in identifying information indicative of callable members for use in calling members for scheduling of appointments, e.g., on a daily and/or hourly basis.

In operation, call list engine 127 identifies (702) members that have a notification status (e.g., a mailing status) within a predetermined time period (e.g., the beginning of a year). As previously described, system 116 may send out notification messages to various members to invite them to participate in a health risk assessment. The members who are notified within the predefined time period are included in an initial list of members to consider for calling.

Call list engine 127 also filters (704) members who are included in the initial list. For example, call list engine 127 excludes member that have had a completed visit disposition within a predefined time period (e.g., in the last 180 days, in the current year, and so forth). Call list engine 127 also excludes members that have an active scheduled visit appointment with a date in future or past. Call list engine 127 also excludes members that do not have a valid format phone number (e.g., not in 10 digit format). Call list engine 127 also excludes members that have one or more of the following as a disposition status since the latest notification date, e.g., a disposition status of declined, a disposition status of deceased, a disposition status of customer excluded, a disposition status of are in pending verification status, a disposition status of requested remove from call list, a disposition status of having recently declined an invitation (e.g., in the last 60 days), a disposition status of having exceeded a maximum call limit since last notification and/or scheduled visit, a disposition status of having a telephone with a busy signal more than predetermined number of times, a disposition status of a non-busy answer (no answer, left message, and so forth) more than a predetermined number of times, a disposition status of not being eligible for a health risk assessment, and so forth.

In the example of FIG. 7, call list engine 127 compares the filtered members to members who are already in a list of callable members to determine (705) if a member is already in the list of callable members. If the member is already in the list of callable members, call list engine 127 updates (706) an eligibility status of the member (in member state information to indicate that the member is eligible for a HRA), if necessary. If the existing data record for the member specifies that the member is ineligible for an HRA and the new callable member list includes the member, the existing record is updated to reflect a status of eligible for a HRA. If the member is not already in the list of callable members, call list engine 127 updates (708) the list of callable members by adding the member to the list of callable members.

In an example, CCA 125 includes call list engine 127 which provides a periodic (e.g., continuous) feed to outbound call agents to reach out to the member for scheduling a visit with a recommended best slot in order to achieve a better health care provider (e.g., a nurse practitioner) utilization and driving route to visit the members. In an example, the call list engine 127 randomly calls members. In this example, the member to be called for a certain slot for a health care provider is randomly picked (e.g., by the call list engine 127) to distribute the calls evenly across the booking window. The call list engine 127 also is configured to take into account the fact that the availability of health care providers change. To capture the latest health care provider availabilities, call list engine 127 provides availability overrides to perform the calendar slots adjustment, creating new calendar slots if the availabilities increased or deleting the calendar slots if the availabilities decreased. If the calendar slot is deleted, the associated already scheduled visits are marked as "pending" by call list engine 127 to require an action to cancel, reschedule or "leave it as is".

As shown in the below Table 3, a slot in a schedule (e.g., slot 542 in schedule 540 in FIG. 5B) is associated in data repository 126 with a data record that specifies "calendar slot status type," including, e.g., information indicative of a state of a particular slot. There are various types of calendar slot status types, including, e.g., an active type and a deleted type. In an active type, the slot is available to be scheduled with an appointment and system 116 executes the geo-dialing algorithm to schedule the appointment. In a deleted type, the slot is not available for appointments and appointments that have already been scheduled for that slot are rescheduled or cancelled.

TABLE 3

| Calendar slot status | typeActive |
| --- | --- |
| | Deleted |

As shown in the below Table 4, when a member schedules an HRA, member state information (and/or other data records stored in data repository 126) is updated with scheduled visit status type, e.g., information indicative of a state of scheduled visits. There are various scheduled visit status types, including, e.g., a status type of scheduled and a status type of pending. A status type of pending requires system 116 to perform an action for the appointment, e.g., canceling the appointment, re-scheduling the appointment, and leaving the appointment as is.

TABLE 4

| Scheduled visit status type | Scheduled |
| --- | --- |
| | Pending (Cancel, Re-schedule, Leave as is) |

Call list engine 127 also enables changes to start locations and zone coverages. To capture the updated health care provide start locations and zone coverages, which will impact the already scheduled visits when a health care provider is no longer in that area for the target scheduled date. These already scheduled visits will be marked as pending as health care provider start locations and zone coverages are modified.

Call list engine 127 also accounts for overbooking. The overbooking occurs in various forms due to multiple scheduling systems, e.g., with thirty minutes sync periods among these systems. In this example, each system does not know an occurrence of overbooking while scheduling a visit due to the availabilities on their local environments until the sync occurs among the multiple systems, e.g., when system 116 includes a distributed computing environment with numerous, different CCAs 125 and call list engines 127. Call list engine 127 schedules a batch sync operation (e.g., an operation to sync scheduled appointment slots), e.g., to capture the overbooking based on the latest availabilities. If the total utilized calendar slots exceed the total availabilities, call list engine 127 marks the most recently generated scheduled visits as the overbooking visits. In this case, an overbooked visit is updated to have a pending scheduled visit status type and a deleted calendar slot status type.

In this example, when a member is scheduled for a health risk assessment, member state information for the member is updated. When a member is scheduled for a health risk assessment, a slot in a calendar or a schedule is also updated, e.g., via the calendar slot status type. When a member is scheduled for a health risk assessment, the scheduled visit status type for the member is also updated In an example, call list engine 127 is configured to generate a report (e.g., from records stored in data repository 126) to select the "pending" scheduled visit status types in order to generate a notification (e.g., for a user of system 116) to require one or more of the following actions, e.g., a cancel action, a rescheduled action and a leave it as is action. These actions promote a user to take action with regarding to overbooking A cancel action is to cancel scheduled visits and to release the calendar slot if it is not marked as deleted. A rescheduled action is to reschedule scheduled visits and release the calendar slot if it is not marked as rescheduled. A leave it as is action specifies that no action is required and the scheduled visits will remain as valid scheduled visits.

In an example, call list engine 127 is configurable to specify a number of days (e.g., a maximum) until the schedule is generated (e.g., "max days to schedule"). In an example, the health care provider calendar slots (e.g., slots in a calendar) are generated for a predefined number of days (e.g., next 10 days) and members can be scheduled for that period. In another example, the number of days is configurable and may be modified dynamically. In this example, if the number of days is increased, call list engine 127 generates the calendar slots for the additional days and assigns members to contact for those new slots to a call queue to promote scheduling of these new slots. If the number of days is reduced, call list engine 127 leaves scheduled appointments unchanged in the days that are removed and also keeps the slots for those days. In this example, call list engine 127 adjusts the call queue to present slots within the updated "max days to schedule".

Call list engine 127 is also configured to adjust client priority (e.g., priority with which members are called to schedule health risk assessments) by mileage and/or by density. In an example, call list engine 127 determines a priority of members to call based on the shortest distance between a geographic location of the health care provider and geographic locations of members. In this example, to increase a priority for calling a particular member, a distance offset is applied to the distance between the geographic location of the health care provider and the geographic location of the particular member, with the distance offset decreasing the distance, which in turn increases a priority with which the particular member is called. For example, the members for a higher priority client (e.g., insurance company) in a particular state are called first provided the distance is within a particular limit (e.g., radial distance for a provider). The adjusted distance is actual distance+/−an offset depending on client and member state.

Call list engine 127 prevents multiple users calling for same calendar slot. In an example, call list engine 127 limits a number of members being called for a specific slot to a value of one or a configurable value.

Call list engine 127 enables deactivation of a value specifying that health risk assessments may be scheduled with a particular health care provider. Call list engine 127 may do so to concentrate scheduling of appointments with other health care providers and to prevent the scheduling of appointments with certain other health care providers. The deactivated health care providers are not considered by the call list engine 127 for outbound users, e.g., call agents who are making or otherwise participating in calls with members. However, inbound users (e.g., members) are able to view availability and book scheduled visits for the deactivated health care providers.

Figure 8:
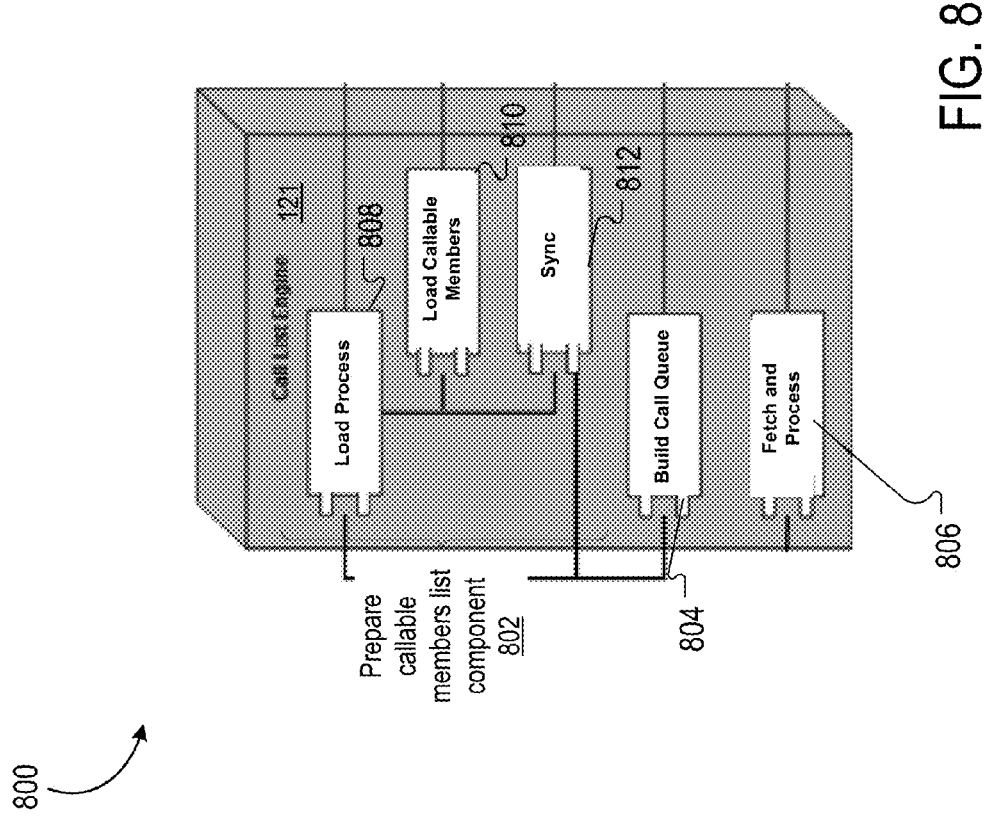
FIG. 8 is a block diagram of components of a call list engine.

Referring to FIG. 8 component architecture 800 of call list engine 127 is shown. In this example, call list engine includes a prepare callable members list component 802 that includes instructions to execute a scheduled (e.g., daily) job to identify callable members, as well as retrieve from data repository 126 information indicative of supported geographic zones, health care provider calendars, and start locations of the health care providers. The job can also be scheduled to run multiple times daily or executed on an ad hoc basis to address any urgent need for callable members.

Call list engine 127 includes build call queue component 804 that includes instructions to execute a job that is scheduled to run at predefined times (e.g., every minute) during call center operation hours in order to build the call queue for each logged in outbound user (e.g., a call agent) for fetching next member to reach out to. Call list engine 127 includes fetch and process component 806 that includes a user interface (UI) application to fetch (e.g., retrieve) the member from the top of a call queue and try to reach out (e.g., call) for scheduling a visit.

The prepare callable members list component 802 includes processes 808, 810, 812 that can be run independently of each other and more frequently as following. Daily load process 808 is executed at predefined times (e.g., daily) and generates a healthcare provider calendar (e.g., calendar with slots for the scheduling of health risk assessment). Load process 808 also executes load callable members process 810 and health care provider sync process 812.

In this example, health care provider sync process 812 performs a synchronization of the geographic zones and the health care provider start location and zone coverage, e.g., to re-evaluate the existing calendar slots and already scheduled visits. As health care provider start locations and availability may change during the day, health care provider sync process 812 may be run more often, scheduled or on demand. In an example, this process is based on the latest health care provider availabilities/availability overrides and the start location to perform the calendar slots and already scheduled visits adjustment. If some calendar slots are no longer available, the associated scheduled visits are marked as pending to require the system 116 to take an action (e.g., cancel, reschedule, or leave it as it.

As previously described, the health care provider sync process 812 performs the adjustment of calendar slots and already scheduled visits due to the changes in health care provider availabilities and start location. In this example, health care provider sync process 812 adjusts the calendar slots based on the latest availabilities and overrides, e.g., when slots increased, add new calendar slots and when slots decreased, remove the extra calendar slots that have open status by updating them to delete status. If open calendar slots have been consumed, then mark the already scheduled visits as pending status and calendar as delete status. Pending scheduled visits with deleted calendar slots are the overbooking (e.g., the overbooked slots). The health care provider sync process 812 adjusts already scheduled visits due to the change of health care provider start location and zone coverage In this example, the load callable members process 810 loads the callable members into the call member list. The load callable members process 810 is included in load process 808 and can be executed on demand if the amount of callable members is low and needs to be refilled.

Process 808 loads callable members into a list and also populate sa call member details table (e.g., a table for storage and display of member information to assist an agent in calling a member to schedule a health risk assessment) with member demographic, address and phone information. The call member details table is updated for members with newer data and also new records are inserted.

Figure 9:
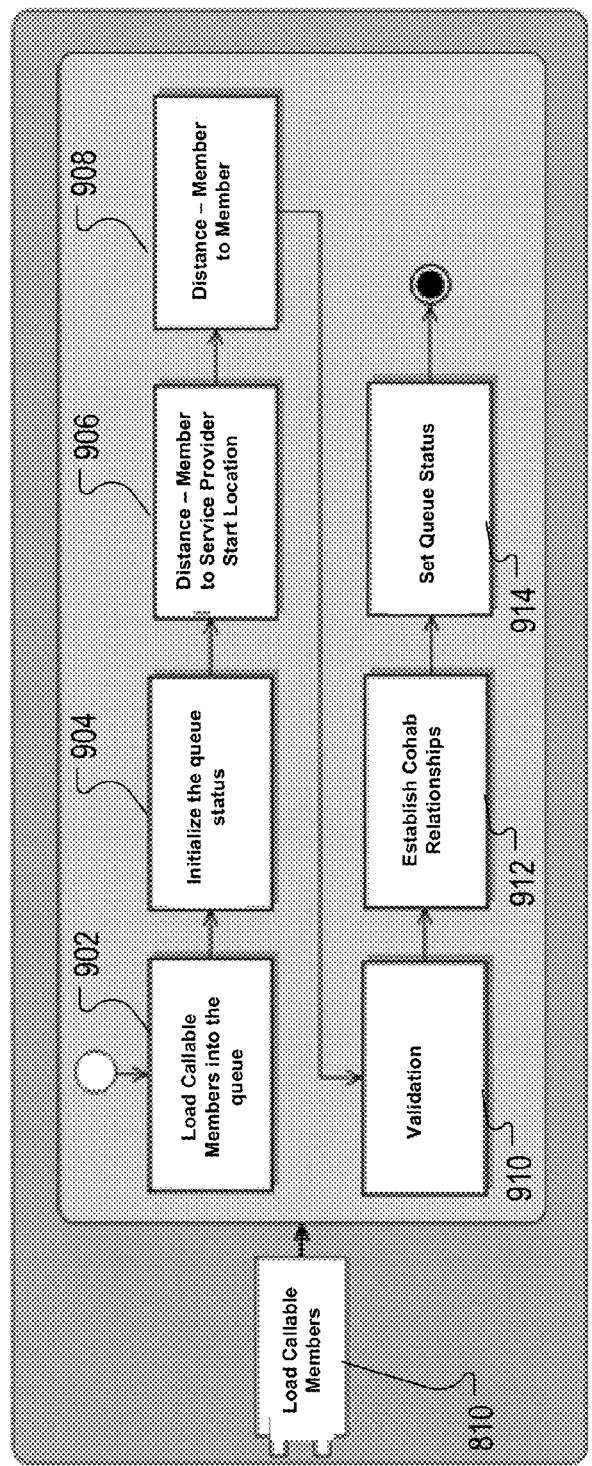

Referring to FIG. 9 operations included in load callable members process 810 are shown. In an example, call list engine 127 loads (902) callable members into a queue or a list and also populates a call member details table (e.g., a table for storage and display of member information to assist an agent in calling a member to schedule a health risk assessment) with member demographic, address and phone information. The call member details table is updated for members with newer data and also new records are inserted.

Call list engine 127 also initializes (904) and/or re-initializes a list status for each member in order to re-evaluate the member demographics information. In an example, a list status has a value of "complete" if a member is associated with a scheduled status (e.g., a value specifying that the member has successfully scheduled an appointment). In this example, a member with a queue list of complete is deleted from the callable members list or otherwise not called. As described herein, the callable members list may be different from a call scheduled visits table that includes information indicative of statuses of scheduled appointments and visits. In another example, a list status has a value of "incomplete" if a member has not yet been successfully scheduled for an appointment. Members with incomplete statuses remain on the callable members list.

Call list engine 127 determines (906) a distance from a geographic location of a member to a health care provider start location. This action is to determine health care providers who can visit the target members (from members represented in the call list) based on the zip code of members and based on zone linkage (e.g., whether a health care provider is assigned to a zone that encompasses a geographic location of a member) and to calculate the distance (between a geographic location of a health care provider and a geographic location of a member) in order to select a member that is geographically located closest to the provider.

Call list engine 127 also determines (908) a distance from member to member. In action 908, call list engine 127 determines already scheduled members who can be considered to be in the same route with the target members (from the callable members that are loaded into the call queue.) In an example, for each targeted callable member, call list engine 127 calculates a distance between a geographic location of a targeted callable member and a geographic location of a scheduled member (who is already scheduled for an appointment in a calendar). In this example, if a member already has a scheduled appointment with a health care provider, for appointments that are subsequent to this scheduled appointment, the starting location of health care provider is the geographic location of this scheduled appointment. Accordingly, in generating the call queue, call list engine 127 determines targeted members with shortest distances to geographic locations of scheduled appointments.

In an example, call list engine 127 also validates (910) the phone number of the member by confirming that the phone number includes a specified number of digits. Call list engine 127 also determines (912) whether target members on the callable member list are in co-habitation arrangements. To make this determination, call list engine 127 removes the suffix in a last name of a member (e.g., in the member details table described above). Call list engine 127 identifies cohabitation relationships by detecting in the member details table entries with a same last name, a same telephone number and/or a same geographic location (which may be identified by a geocode). Generally, a geocode includes information indicative of geographic coordinates (often expressed as latitude and longitude) that are derived from other geographic data (e.g., a street name and city). For members that are in a cohabitation relationship, call list engine 127 schedules appointments for these members in a same time slot. Call list engine 127 also sets (914) a status of the callable member list to be "ready," e.g., when the callable member list is ready to be used in generating the call queue.

In this example, upon completion of load callable members, call list engine 127 generates for a particular health care provider a list of eligible members who are within a geographic zone that is assigned to the particular health care provider and who are also eligible for a health risk assessment. In this example, the particular health care provider is associated with a schedule that includes a plurality of time slots. In this example, at least some of the time slots are already scheduled. To promote scheduling of new appointments that are in proximity to already scheduled appointments, call list engine 127 computes distances between geographic locations of callable members and the geographic location of a member who is already scheduled for an appointment.

Figure 10:
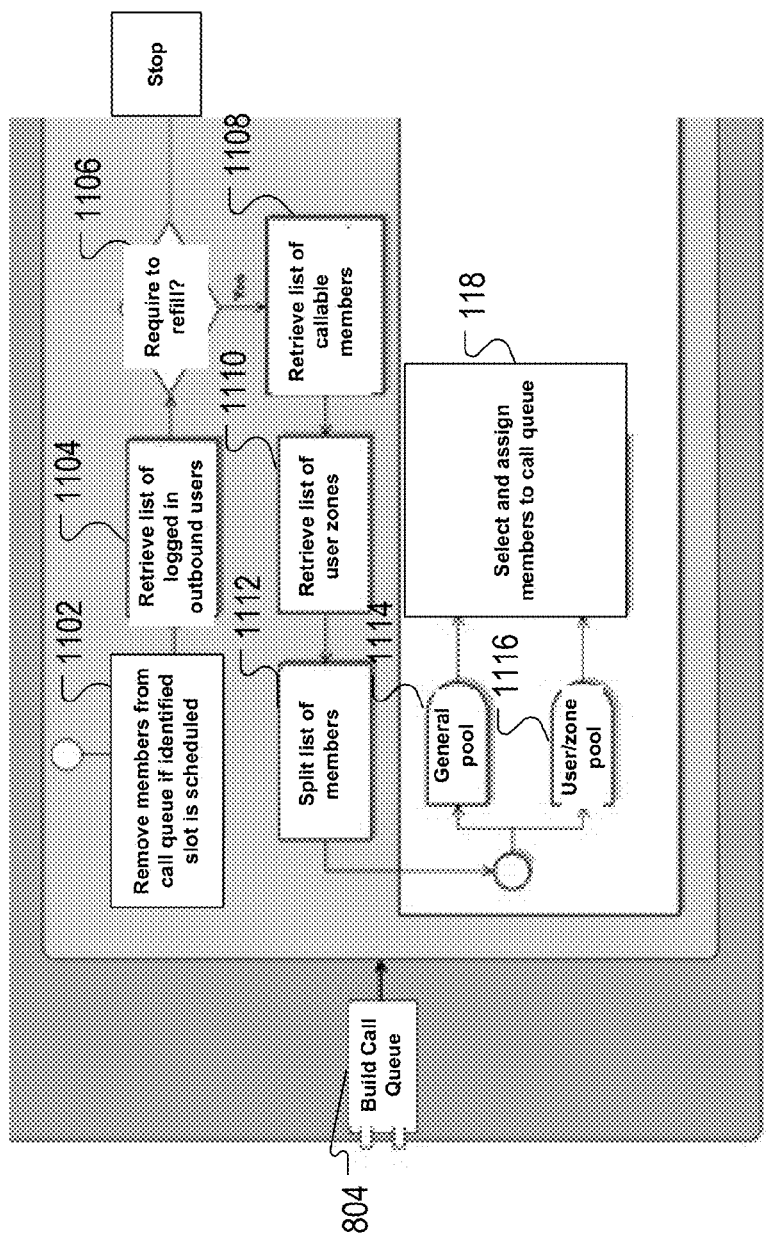

Referring to FIG. 10 various actions that are executed as part of process 804 for generating a call queue, e.g., using the list of callable members are shown. As previously described, the build call queue process 804 generates a queue of members to call for particular slots within a schedule, e.g., by presenting slots within a "max days to schedule".

In the example of FIG. 10, call list engine 127 removes (1102) members from the call queue, if an identified slot (e.g., a best slot for those members) is no longer available. Generally, a best slot includes a slot in a schedule for which a member has been identified as being a candidate for being scheduled for an appointment for that slot, e.g., based on distance between a geographic location of the member and a geographic location of an appointment that is scheduled for a time prior to the time associated with the slot. Information indicative of these members are placed in the list of callable members and is re-evaluated by the build call queue process 804 again to determine the best slot.

Call list engine 127 also retrieves (1104) a list of logged in outbound users, e.g., to identify logged in outbound users. An outbound user includes an agent at a call center. In this example, call list engine 127 also retrieves, e.g., from data repository 126, information indicative of a count of empty call slots in each logged in user's call queue to be filled. For a call agent, the agent has a specified number of call slots indicative of calls to be made while the agent is working. In this example, an outbound agent includes an individual at a call center (or other operation) who places calls to members to promote scheduling of appointments. A user is associated with a particular call queue (or call list), e.g., a listing of members to call for particular slots in schedules of a particular health care provider. In an example, a call queue may already be partially populated, e.g., based on a prior execution of build call queue process 804. A call queue may also include empty slots, e.g., when a member that was previously identified as a candidate for calling becomes ineligible for a health risk assessment or is otherwise removed from the call queue, as shown in the below Table 4.

TABLE 4

| SCHEDULE | | PROVIDER CALL QUEUE | |
|---|---|---|---|
| DATE | TIME SLOT | Call queue slot | Members to call |
| Oct. 1, 2013 | 1 PM | 1 | Member ID 1234<br>Member ID 1235<br>Member ID 1236<br>[EMPTY] |
|  | 2 PM | 2 | Member ID 2234<br>Member ID 2235<br>Member ID 2236<br>[EMPTY] |

As shown in the above Table 4, a schedule (e.g., for a particular health care provider), includes various time slots (e.g., a 1 pm time slot and a 2 pm time slot) for a particular date (e.g., 10/1/2013). In this example, a call queue (e.g., a provider call queue) is also associated with call queue slots. In this example, call list engine 127 assigns a time slot in the schedule to a call queue slot in the call queue. For a call queue slot, call list engine 127 identifies various members to call, e.g., using the techniques described herein. In the example shown above, the 1 pm time slot is assigned the first slot in the call queue. In this example, call list engine 127 has identified various members to be called to schedule appointments, e.g., these members include members who are identifiable by various member IDs (e.g., member IDs 1234, 1235, 1236). In this example, the first call queue slot includes an empty slot. Using the techniques described herein, call list engine 127 executes various processes to fill the empty slot. In some example, a particular slot in a call queue may be entirely empty (e.g., when no members have been identified to be called for that slot).

In an example, call list engine 127 may also generate a multi-provider call queue, when a call agent schedules appointments for multiple, different providers, e.g., rather than scheduling appointments for a particular provider. An example of a multi-provider call queue is provided in the below Table 5:

TABLE 5

| SCHEDULE | | MULTI-PROVIDER CALL QUEUE | |
|---|---|---|---|
| DATE AND PROVIDER ID | TIME SLOT | Call queue slot | Members to call |
| Oct. 1, 2013 for Provider ID: 1245 | 1 PM | 1 | Member ID 1234<br>Member ID 1235<br>Member ID 1236<br>[EMPTY] |
| Oct. 1, 2013 for Provider ID: 1246 | 1 PM | 2 | Member ID 2234<br>Member ID 2235<br>Member ID 2236<br>[EMPTY] |
| Not yet assigned | Not yet assigned | 3 | EMPTY |

As shown in the above Table 5, the multi-provider call queue also includes various slots to be filled for various different providers, e.g., a provider identified by provider ID 1245 and a provider identified by provider ID 1246. In this example of Table 5, the first slot in the multi-provider call queue is for the provider identified by provider ID 1245 and the second slot in the multi-provider call queue is for the provider identified by provider ID 1246. Within each slot in the call queue, the members to be called to schedule an appointment for a particular time slot are prioritized, e.g., based on distance between a geographic location of the member and based on a geographic location of a health care provider and/or based on a geographic location of a prior appointment of the health care provider.

As shown in the above Table 5, the third slot in the multi-provider call queue has not yet been assigned. In this example, call list engine 127 executes the below described actions to identify which members to call to schedule for the third slot.

In the example of FIG. 10, call list engine 127 determines (1106) whether a call queue (e.g., a multi-provider call queue) (and/or particular slots within a call queue) are empty and require filling (or re-filling). When call list engine 127 determines that a call queue requires refilling, call list engine 127 retrieves (1108) a full list of callable members for particular calendar slots. In this example, call list engine 127 determines combinations of calendar slots for callable members via randomized best slots logic as following. In this example, call list engine 127 retrieves (1108) a list of callable members. As previously described, the list of callable members may specify which members are eligible for a health risk assessment. In this example, call list engine 127 retrieves the members from the list of callable members who are listed as being eligible. As previously described, for a member, data repository 126 stores a record for that member (e.g., in a profile for the member). This record may be referred as a member record. In this example, the member record includes a member ID that uniquely identifies the member. The member record also includes other identifying information for a member, including, e.g., a zip code of the member. The callable member list also identifies members by the member ID.

For the callable members, call list engine 127 retrieves from data repository 126, the member records and identifies in the member records the zip codes for the members on the callable member list. As previously described, a call queue may be specific to a particular health provider, e.g., a call queue is for and associated with the particular health care provider. In this example, each health care provider is associated with his/her own call queue. For a health care provider participating in the system, data repository 126 also stores a health care provider record that includes identifying information of a health care provider, e.g., zip codes of the health care providers.

Call list engine 127 retrieves information indicative of health care providers who (i) are located within the zip codes that are associated with the members in the callable members list, and (ii) have available time slots in his/her calendar. In this example, call list engine 127 determines callable members who are in the local operation hours (e.g., local time 8 am-8 pm) and updates the callable members list to include these callable members.

For an available slot in the health care providers' schedules, call list engine 127 identifies a member (from the updated callable members list) with a shortest distance to the health care provider. Call list engine 127 also adjusts the shortest distance for any offset distance based on priorities of various clients (e.g., insurance companies and/or individual members). For an available slot with the closest calendar date to the current date, call list engine 127 selects a predefined number of members that are closest to the geography location of the health care provider associated with the slot for the closest calendar date. Call list engine 127 populates the empty slot in the call queue with these predefined members, e.g., to promote scheduling of the empty slot with an appointment.

In another example, call list engine 127 executes additional actions (as described below), prior to populating a call queue. In the example of FIG. 10, call list engine 127 also retrieves (1110) from data repository 126 a list of user zones to identify specific members in the zone where user (e.g., a call agent and/or a health care provider) has been assigned to. In this example, a call agent is assigned to specific geographic zones (e.g., locations), e.g., to promote even load distribution of calls. To further promote more even calling of available members, call list engine 127 splits (1112) the updated list of callable member into a user zone pool 1114 and a general pool 1116.

In this example, call list engine 127 assigns the members with zip codes that are included in (or otherwise associated with) the user zone to user zone pool 116. Call list engine 127 assigns the remaining members (or a portion there) to the general pool.

In this example, call list engine 127 assigns (1118) members from one or more of the general pool 114 and the user zone pool 1116 to the call queue based on one or more of the following actions. In this example, call list engine 127 selects a calendar date for which to schedule appointments (for multiple, different providers). In some examples, call list engine 127 randomly selects this calendar date. In other examples, call list engine 127 receives instructions (e.g., from a user) that specify a particular calendar date. For the selected calendar date, call list engine 127 identifies the available slots (e.g., available slots in health care providers' schedules for that day). In this example, call list engine 127 may identify the available slots in a predefined order (e.g., a descending order) based on particular times that are associated with the slots. For an identified particular slot, call list engine 127 identifies one or more callable members to fill the slot based on callback request time and distance. In this example, a member may specify a time at which the member wants to be called to called to schedule an appointment. For example, a member may specify that he/she wants to be called at 2 pm to schedule an appointment. In this example, if the identified particular slot is for 2 pm, then call list engine 127 may select a member with a requested callback time of 2 pm or a requested call back time that is close to 2 pm. In still another example, call engine 127 may select a member based on proximity of a geographic location of the member to a geographic location of a health care provider.

In this example, call list engine 127 may identify a callback variance, e.g., an amount by which a requested call back time (if any) varies from a time associated with the slot. Call list engine 127 may also identify a distance variance, e.g., an amount of distance between a geographic location of a member and a geographic location of health care provider (e.g., from either a starting location and/or from a prior scheduled appointment). In this example, call list engine 127 is configured to compute a priority value, e.g., based on the callback variance and the distance variance. In an example, the priority value is the sum of the callback variance and the distance variance. The priority values include a value indicative of a priority (e.g., ranking) at which members should be called to schedule a particular slot. A member with a lowest priority value is ranked with a higher priority, e.g., relative to other priority values of other members. In this example, a member with the lowest priority value for the time slot is loaded into the queue and called first in the queue. In an example, call list engine 127 selects, from general pool 114 and from user zone pool 116, members associated with lowest priority values and populates a slot in the queue with those users.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data.

Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be data in different formats such as text, graphics, images, sound, video, Hypertext Markup Language (HTML), as well as programs. Upon specification of a link by the user, the client computer makes a TCP/IP request to a Web server and receives data, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view data available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method comprising:
identifying, in a data repository, (i) information indicative of a health care provider who is assigned to a pre-defined calling zone, and (ii) radius information indicative of a radial distance from a starting location that the health care provider will travel to perform a health risk assessment;
accessing scheduling information that comprises a plurality of time slots, wherein each time slot corresponds to a time for the health care provider to perform the health risk assessment;
automatically selecting, using one or more computer systems, a particular slot from the scheduling information;
determining that a particular candidate is required to be prioritized in scheduling of health risk assessments;
retrieving, using one or more computer systems from the data repository, a distance offset value that is associated with the particular candidate, with the distance offset value specifying an amount by which a distance between a geographic location of the particular candidate and a geographic location of the health care provider is decreased to promote scheduling of a health risk assessment for the particular candidate before scheduling of health risk assessments for other clients;
for the selected slot,
computing using one or more computer systems distances between geographic locations of candidates and the geographic location of the health care provider;
applying the distance offset value to a computed distance for the particular candidate;
decreasing, using one or more computer systems based on applying the distance offset value, an amount of the computed distance between the geographic location of the health care provider and the geographic location for the particular candidate; and
increasing, using one or more computer systems based on the decreased computed distance, a priority of the particular candidate for scheduling with the health care provider;
applying a geo-dialing algorithm to computed distances with applied one or more distance offset values and candidate information that is indicative of one or more members of one or more health plans who are candidates for scheduling in the selected time slot;

identifying, using one or more computer systems based on application of the geo-dialing algorithm, a candidate with a geographic location that is a decreased distance from a geographic location of the health care provider, relative to other distances of other candidates from the health care provider;

comparing using one or more computer systems (i) an amount of distance between the geographic location of the identified candidate and the starting location of the health care provider, to (ii) the radial distance;

confirming, using one or more computer systems and based on comparing, that the geographic location of the identified candidate is within the radial distance; and causing a call to be placed to the identified candidate to promote scheduling of the health risk assessment between the identified candidate and the health care provider at a time that is associated with the selected slot.

2. The computer-implemented method of claim 1, further comprising:

retrieving a priority call queue, with the priority call queue specifying an order in which the one or more computer systems place calls to candidates in accordance with distances between geographic locations of the candidates and the geographic location of the health care provider;

wherein identifying the candidate comprises identifying a candidate ranked first in the priority call queue.

3. The computer-implemented method of claim 1, further comprising repeating the actions of selecting a slot, applying the geo-dialing algorithm, identifying a candidate and causing a call to be placed until each of the slots in the scheduling information is populated with scheduling information.

4. The computer-implemented method of claim 1, wherein the identified candidate is a first identified candidate, the amount of distance is a first amount of distance, and wherein the method further comprises:

determining that a second amount of distance between a geographic location of a second identified candidate and the starting location of the health care provider is greater than the radial distance;

determining that the second identified candidate is ineligible to be seen by the health care provider; and replacing the ineligible candidate with another candidate who is associated with a geographic location that is a decreased distance from the geographic location of the health care provider, relative to other distances of other candidates from the health care provider.

5. The computer-implemented method of claim 1, further comprising receiving acceptance information specifying that the candidate has scheduled the health risk assessment;

updating the selected slot with identifying information for the candidate to schedule the health care provider to perform the health risk assessment at a time associated with the selected slot;

updating the geographic location of the health care provider to be the geographic location of the candidate who scheduled the appointment;

selecting another slot from the scheduling information, with the selected other slot being a next slot in the scheduling information;

for the selected other slot, identifying another candidate with a geographic location that is a decreased distance from the updated geographic location of the health care provider, relative to other distances of other candidates from the health care provider; and causing a call to be placed to the identified other candidate.

6. One or more machine-readable hardware storage devices storing instructions that are executable by one or more processing devices to perform operations comprising:

identifying, in a data repository, (i) information indicative of a health care provider who is assigned to a pre-defined calling, and (ii) radius information indicative of a radial distance from a starting location that the health care provider will travel to perform a health risk assessment;

accessing scheduling information that comprises a plurality of time slots, wherein each time slot corresponds to a time for the health care provider to perform the health risk assessment;

automatically selecting a particular slot from the scheduling information;

determining that a particular candidate is required to be prioritized in scheduling of health risk assessments;

retrieving, from the data repository, a distance offset value that is associated with the particular candidate, with the distance offset value specifying an amount by which a distance between a geographic location of the particular candidate and a geographic location of the health care provider is decreased to promote scheduling of a health risk assessment for the particular candidate before scheduling of health risk assessments for other clients;

for the selected slot, computing distances between geographic locations of candidates and the geographic location of the health care provider;

applying the distance offset value to a computed distance for the particular candidate;

decreasing, based on applying the distance offset value, an amount of the computed distance between the geographic location of the health care provider and the geographic location for the particular candidate; and increasing, based on the decreased computed distance, a priority of the particular candidate for scheduling with the health care provider;

applying a geo-dialing algorithm to computed distances with applied one or more distance offset values and candidate information that is indicative of one or more members of one or more health plans who are candidates for scheduling in the selected time slot;

identifying, based on application of the geo-dialing algorithm, a candidate with a geographic location that is a decreased distance from a geographic location of the health care provider, relative to other distances of other candidates from the health care provider;

comparing (i) an amount of distance between the geographic location of the identified candidate and the starting location of the health care provider, to (ii) the radial distance;

confirming, and based on comparing, that the geographic location of the identified candidate is within the radial distance; and causing a call to be placed to the identified candidate to promote scheduling of the health risk assessment between the identified candidate and the health care provider at a time that is associated with the selected slot.

7. The one or more machine-readable hardware storage devices of claim 6, wherein the operations further comprise:

retrieving a priority call queue, with the priority call queue specifying an order in which calls are placed to candidates in accordance with distances between geographic locations of the candidates and the geographic location of the health care provider;
wherein identifying the candidate comprises identifying a candidate ranked first in the priority call queue.

8. The one or more machine-readable hardware storage devices of claim 6, wherein the operations further comprise: repeating the actions of selecting a slot, applying the geo-dialing algorithm, identifying a candidate and causing a call to be placed until each of the slots in the scheduling information is populated with scheduling information.

9. The one or more machine-readable hardware storage devices of claim 6, wherein the identified candidate is a first identified candidate, the amount of distance is a first amount of distance, and wherein the operations further comprise:
  determining that a second amount of distance between a geographic location of a second identified candidate and the starting location of the health care provider is greater than the radial distance;
  determining that the second identified candidate is ineligible to be seen by the health care provider; and
  replacing the ineligible candidate with another candidate who is associated with a geographic location that is a decreased distance from the geographic location of the health care provider, relative to other distances of other candidates from the health care provider.

10. The one or more machine-readable hardware storage devices of claim 6, wherein the operations further comprise:
  receiving acceptance information specifying that the candidate has scheduled the health risk assessment;
  updating the selected slot with identifying information for the candidate to schedule the health care provider to perform the health risk assessment at a time associated with the selected slot;
  updating the geographic location of the health care provider to be the geographic location of the candidate who scheduled the appointment;
  selecting another slot from the scheduling information, with the selected other slot being a next slot in the scheduling information;
  for the selected other slot,
    identifying another candidate with a geographic location that is a decreased distance from the updated geographic location of the health care provider, relative to other distances of other candidates from the health care provider; and
    causing a call to be placed to the identified other candidate.

11. An electronic system comprising:
  one or more processing devices; and
  one or more machine-readable hardware storage devices storing instructions that are executable by the one or more processing devices to perform operations comprising:
    identifying, in a data repository, (i) information indicative of a health care provider who is assigned to a pre-defined calling, and (ii) radius information indicative of a radial distance from a starting location that the health care provider will travel to perform a health risk assessment;
    accessing scheduling information that comprises a plurality of time slots, wherein each time slot corresponds to a time for the health care provider to perform the health risk assessment;
    automatically selecting a particular slot from the scheduling information;
    determining that a particular candidate is required to be prioritized in scheduling of health risk assessments;
    retrieving, from the data repository, a distance offset value that is associated with the particular candidate, with the distance offset value specifying an amount by which a distance between a geographic location of the particular candidate and a geographic location of the health care provider is decreased to promote scheduling of a health risk assessment for the particular candidate before scheduling of health risk assessments for other clients;
    for the selected slot,
      computing distances between geographic locations of candidates and the geographic location of the health care provider;
      applying the distance offset value to a computed distance for the particular candidate;
      decreasing, based on applying the distance offset value, an amount of the computed distance between the geographic location of the health care provider and the geographic location for the particular candidate; and
      increasing, based on the decreased computed distance, a priority of the particular candidate for scheduling with the health care provider;
      applying a geo-dialing algorithm to computed distances with applied one or more distance offset values and candidate information that is indicative of one or more members of one or more health plans who are candidates for scheduling in the selected time slot;
      identifying, based on application of the geo-dialing algorithm, a candidate with a geographic location that is a decreased distance from a geographic location of the health care provider, relative to other distances of other candidates from the health care provider;
      comparing (i) an amount of distance between the geographic location of the identified candidate and the starting location of the health care provider, to (ii) the radial distance;
      confirming, and based on comparing, that the geographic location of the identified candidate is within the radial distance; and
      causing a call to be placed to the identified candidate to promote scheduling of the health risk assessment between the identified candidate and the health care provider at a time that is associated with the selected slot.

12. The electronic system of claim 11, wherein the operations further comprise:
  retrieving a priority call queue, with the priority call queue specifying an order in which calls are placed to candidates in accordance with distances between geographic locations of the candidates and the geographic location of the health care provider;
  wherein identifying the candidate comprises identifying a candidate ranked first in the priority call queue.

13. The electronic system of claim 11, wherein the operations further comprise: repeating the actions of selecting a slot, applying the geo-dialing algorithm, identifying a candidate and causing a call to be placed until each of the slots in the scheduling information is populated with scheduling information.

14. The electronic system of claim 11, wherein the identified candidate is a first identified candidate, the amount of distance is a first amount of distance, and wherein the operations further comprise:
- determining that a second amount of distance between a geographic location of a second identified candidate and the starting location of the health care provider is greater than the radial distance;
- determining that the second identified candidate is ineligible to be seen by the health care provider; and
- replacing the ineligible candidate with another candidate who is associated with a geographic location that is a decreased distance from the geographic location of the health care provider, relative to other distances of other candidates from the health care provider.

15. The electronic system of claim 11, wherein the operations further comprise:
- receiving acceptance information specifying that the candidate has scheduled the health risk assessment;
- updating the selected slot with identifying information for the candidate to schedule the health care provider to perform the health risk assessment at a time associated with the selected slot;
- updating the geographic location of the health care provider to be the geographic location of the candidate who scheduled the appointment;
- selecting another slot from the scheduling information, with the selected other slot being a next slot in the scheduling information;
- for the selected other slot,
    - identifying another candidate with a geographic location that is a decreased distance from the updated geographic location of the health care provider, relative to other distances of other candidates from the health care provider; and
- causing a call to be placed to the identified other candidate.

* * * * *